United States Patent
Bray et al.

(10) Patent No.: US 12,391,974 B2
(45) Date of Patent: Aug. 19, 2025

(54) METHODS OF DETECTING ALLOANTIBODIES TO HLA CLASS II ANTIGENS

(71) Applicants: EMORY UNIVERSITY, Atlanta, GA (US); ONE LAMBDA, INC., West Hills, CA (US)

(72) Inventors: Robert A. Bray, Snellville, GA (US); Jar-How Lee, Los Angeles, CA (US)

(73) Assignees: Emory University, Atlanta, GA (US); One Lambda, Inc., West Hills, CA (US)

(*) Notice: Subject to any disclaimer, the term of this patent is extended or adjusted under 35 U.S.C. 154(b) by 456 days.

(21) Appl. No.: 17/932,600

(22) Filed: Sep. 15, 2022

(65) Prior Publication Data

US 2023/0029386 A1 Jan. 26, 2023

Related U.S. Application Data

(62) Division of application No. 16/549,321, filed on Aug. 23, 2019, now abandoned.

(60) Provisional application No. 62/722,042, filed on Aug. 23, 2018.

(51) Int. Cl.
*G01N 33/68* (2006.01)
*C07K 14/74* (2006.01)
*C12N 15/85* (2006.01)
*C12Q 1/68* (2018.01)
*G01N 33/554* (2006.01)

(52) U.S. Cl.
CPC .......... *C12Q 1/68* (2013.01); *C07K 14/70539* (2013.01); *C12N 15/85* (2013.01); *G01N 33/554* (2013.01); *G01N 33/6854* (2013.01); *C12N 2015/8518* (2013.01)

(58) Field of Classification Search
None
See application file for complete search history.

(56) References Cited

U.S. PATENT DOCUMENTS

| | | |
|---|---|---|
| 9,250,247 B2 | 2/2016 | Lee et al. |
| 9,354,238 B2 | 5/2016 | Terasaki et al. |
| 2007/0037195 A1 | 2/2007 | Ho |

FOREIGN PATENT DOCUMENTS

WO WO-9014363 A1 11/1990

OTHER PUBLICATIONS

McCaughan et al (HepatoBiliary Surg Nutr, 2019, 8(1): 37-52) (Year: 2019).*
Khan and Salunke (J. Immunol, 2014, 192: 5398-5405) Year: 2014.
Lloyd et al. (Protein Engineering, Eng. Design & Selection, 2009, 22(3): 159-168) Year: 2009.
Poosaria et al. (Biotechn. Bioeng., 2017, 114(6): 1331-1342): Year: 2017.
Roche et al. (EMBO J. 1992, 11(8): 2841-2847) Year: 1992.
Sette et al. (Science, 1992, 258: 1801-1804) Year: 1992.
ATCC LB3.1 (2022, pp. 1/8-8/8) Year: 2022.
Bayer et al., Meth. Enz., 1990, 184, pp. 138-163.
Bix et al., "Functionally conformed free class I heavy chains exist on the surface of beta 2 microglobulin negative cells", J. Exp. Med., vol. 176, No. 3, 1992, pp. 829-834.
Brodeur et al., "Monoclonal Antibody Production Techniques and Applications," 1987, (Marcel Dekker, Inc., New York), pp. 51-63.
Butler M.O., et al., "A Panel of Human Cell-Based Artificial APC Enables the Expansion of Long-Lived Antigen-Specific CD4+ T Cells Restricted by Prevalent HLA-DR alleles," International Immunology, 2010, vol. 22, No. 11, pp. 863-873.
Chao, "The HLA system: genetics, immunology, clinical testing, and clinical implications", Yonsei Med. J., vol. 48, No. 1, 2007, pp. 11-23.
Chen X., et al., "Regulated Expression of Human Histocompatibility Leukocyte Antigen (HLA)-DO during Antigen-dependent and Antigen-independent Phases of B Cell Development," Journal of Experimental Medicine, 2002, vol. 195, No. 8, pp. 1053-1062.
Colvin, Antibody-mediated renal allograft rejection: diagnosis and pathogenesis, J. Am. Soc. Nephrol., 18(4):1046-56 (2007).
Frengen et al., Demonstration and minimization of serum interference in flow cytometric two-site immunoassays, Clin. Chem., 40(3):420-5 (1994).
Kohler., et al., "Continuous Cultures of Fused Cells Secreting Antibody of Predefined Specificity," Nature, Aug. 7, 1975, vol. 256, pp. 495-497.
Krangel et al., "Assembly and maturation of HLA-A and HLA-B antigens in vivo ", Cell, vol. 18, No. 4, 1979, pp. 979-991.
Sambrook et al., "Molecular Cloning: A Laboratory Manual," 1989, Cold Springs Harbor Laboratories (New York), 29 pages.
Sambrook, et al. "Molecular Cloning: A Laboratory Manual", 3rd Edition, Cold Spring Harbor Laboratory Press, N.Y., 2001.
Schnabl et al., "Activated human T lymphocytes express MHC class I heavy chains not associated with beta 2-microqlobulin", J. Exp. Med., vol. 171, No. 5, 1990, pp. 1431-1442.
Scillian J.J., et al., "Early Detection of Antibodies against rDNA-produced HIV Proteins with a Flow Cytometric Assay," Blood, 1989, vol. 73, No. 7, pp. 2041-2048.
Shroyer et al., A rapid flow cytometry assay for HLA antibody detection using a pooled cell panel covering 14 serological crossreacting groups, Transplantation, 59(4):626-30 (1995).
Sumitran-Karuppan et al., The use of magnetic beads coated with soluble HLA class I or class II proteins in antibody screening and for specificity determinations of donor-reactive antibodies, Transplantation, 61 (10):1539-45 (1996).
UniProtKB-P04233 (HG2A_HUMAN), HLA class II histocompatibility antigen gamma chain, CD74, *Homo sapiens*, Retrieved from the Internet: URL: https://www.uniprot.org/uniprot/P04233.

(Continued)

*Primary Examiner* — Misook Yu
*Assistant Examiner* — Marianne Dibrino
(74) *Attorney, Agent, or Firm* — BakerHostetler (57) ABSTRACT

Described herein are materials and methods of incorporating CLIP peptide into the peptide binding groove of HLA Class II antigens and using such HLA Class II antigens for the detection of alloantibodies.

12 Claims, 3 Drawing Sheets

Specification includes a Sequence Listing.

(56) References Cited

OTHER PUBLICATIONS

Urlaub, G., and Chasin, L.A. "isolation of Chinese Hamster cell mutants deficient in dihydrofotlate reductase activity," Proc. Natl. Acad. Sci. USA 77:4216-4220, National Academy of Sciences (1980).

Wilson et al., A new microsphere-based immunofluorescence assay for antibodies to membraneassociated antigens, J. Immunol. Methods, 107(2):231-7 (1988).

Yin L., et al., "Measurement of Peptide Binding to MHC Class II Molecules by Fluorescence Polarization," Current Protocols Immunology, 2014, vol. 106, pp. 5.10.1-5.10.12.

* cited by examiner

METHODS OF DETECTING ALLOANTIBODIES TO HLA CLASS II ANTIGENS

CROSS-REFERENCE TO RELATED APPLICATIONS

This application is a divisional application which claims the benefit of U.S. patent application Ser. No. 16/549,321 filed on Aug. 23, 2019, which claims priority benefit of U.S. Patent Application No. 62/722,042 filed on Aug. 23, 2018, which disclosures are herein incorporated by reference in their entirety.

INCORPORATION BY REFERENCE OF MATERIAL SUBMITTED ELECTRONICALLY

Incorporated by reference in its entirety is a computer-readable sequence listing submitted concurrently herewith and identified as follows: Filename: 52940B_Seq-listing.XML; Size: 3,345 Bytes; Created: Sep. 15, 2022.

FIELD OF THE INVENTION

The present invention is directed to materials and methods for creating HLA Class II antigens to detect alloantibodies by using CLIP and its related precursor CD74 to improve HLA class II antigen quality.

BACKGROUND

Transplant rejection occurs when the immune system of the recipient of a transplant, particularly antibodies produced by the recipient, attacks the transplanted organ or tissue. The recipient's immune system recognizes the transplanted organ as foreign tissue and attempts to destroy it (host vs graft reaction). Rejection also occurs when the transplanted organ consists of donor lymphocytes or progenitor stem cells, which may generate an immune response to the recipient tissues (graft vs. host disease). Chronic rejection is a term used to describe all long term loss of function in organ transplants associated with chronic alloreactive immune response. Chronic rejection usually leads to graft failure and a need for a new transplanted organ about a decade after the initial transplant. Human leukocyte antigens (HLA) are one type of target molecule within a transplanted organ to which the recipient's immune system responds resulting in transplant rejection. The HLA system is highly polymorphic in nature.

It is a standard practice in the transplant field to evaluate all potential recipients for HLA antibodies by testing against a panel of HLA antigens selected to represent an approximate distribution in the human population. In vitro testing determines the specificity of HLA antibodies present in a patient's blood. The detection of HLA antibodies in a patient's serum that are directed against specific HLA alleles present in a potential donor (donor-specific antibody; DSA) is an indication of risk for graft rejection or failure.

Alloantibodies, particularly when donor specific, are one of the most important factors that cause both early and late graft rejection. Despite improvements in transplantation outcomes, antibody-mediated rejection (AMR) remains a significant impediment to long term graft survival and is associated with increased morbidity, mortality and costs (Colvin, A S N 18(4):1046-1056, 2007).

The presence of HLA antibody is widely believed to be one of the major elements contributing to humoral graft rejections. Transplant recipients with high levels of DSA are at risk for with early graft rejection and failure. Elevated donor specific HLA antibodies in organ recipients either before and/or after allograft transplantation has been associated with acute and chronic AMR and decreased long term graft survival.

HIM molecules exist in two forms; HLA class I molecules consist of a 45-kDa glycoprotein (heavy chain) non covalently associated with a 12-kDa polypeptide, $\beta$2-microglobulin ($\beta$2m). Association of $\beta$2m with newly synthesized class I heavy chains is required in order for the HLA molecule to be expressed and present the peptide (Krangel et al., *Cell* 18: 979, 1979). However, $\beta$2m free class I heavy chains were identified on activated T lymphocytes (Schnabl et al., *J. Exp. Med.* 171:1431, 1990) and other cell surfaces (Bix & Raulet, *J. Exp. Med.* 176(3) 829-34, 1992).

HLA class II molecules are heterodimers formed by noncovalent association of two glycosylated polypeptide chains referred to as alpha and beta chains. The $\alpha$ subunit is 33 kDa and the $\beta$ subunit is 28 kDa, and both chains are transmembrane polypeptides that have the same overall structure. The non-polymorphic $\alpha$ chain is encoded by the DRA gene and can associate with various polymorphic $\beta$ chains that are encoded by a specific DRB gene. In addition, the DP and DQ HLA gene families each have one gene that encodes an $\alpha$ chain and a $\beta$ chain. (Reviewed in Choo, *Yonsei Med. J.* 48: 11-23, 2007). During synthesis of class II MHC in the endoplasmic reticulum, the $\alpha$ and $\beta$ chains are produced and complexed with a special polypeptide known as the invariant chain (Ii). See, Chen et al. J. Exp. Med. Vol 195, No. 8, 1053-1062 (2002). The nascent MHC class II protein in the rough endoplastic reticulum has its peptide-binding cleft blocked by the Ii to form a trimer which prevents it from binding cellular peptides or peptides from the endogenous pathway. The Ii chaperone protein associates with folding HLA Class II, occupying the peptide-binding groove and preventing aggregation.

The Ii also facilitates the export of class II MHC from the ER to the golgi, followed by fusion with a late endosome containing endocytosed, degraded proteins. The Ii is then degraded in endosomes by proteases called cathepsins, ultimately leaving only a short Class II-associated invariant chain peptide (CLIP) inside the HLA Class II groove which maintains blockage of the peptide binding cleft on the MHC molecule. An MHC class II-like structure, HLA-DM, facilitates CLIP removal from the groove and allows the binding of peptides with higher affinities. The stable class II MHC is then presented on the cell surface.

The cell surface form of the Ii is known as CD74 (Cluster of Differentiation 74). It is also known as HLA class II histocompatibility antigen gamma chain. There are four major distinct Ii isoforms resulting from alternative splicing during the mRNA transcription process. All of them exhibit similar reactivity. During MHCII $\alpha$ and $\beta$ chains assemble, four Ii isoforms randomly associate into trimers in the ER.

CLIP or Class II-associated-Ii peptide is the part of the Ii that binds HLA class II groove and remains there until the HLA receptor is fully assembled. The purpose of CLIP is to prevent the binding of self-peptide fragments prior to HLA Class II localization within the endo/lysosome. A nested set of Ii peptides, CLIPs (class II-associated Ii peptides), have been eluted from various HLA class II molecules. Although the exact location of the CLIP in the Ii varies, it is generally believed that it is within a region of 40 amino acids with a core sequence of 9 amino acids, MRMATPLLM. (SEQ ID NO: 1) There are various degrees of CLIP associated Class II antigens presented on the B cell surface.

Presentation of antigenic peptides by major histocompatibility complex class II (MHC II) molecules on the cell surface is essential as it evokes different immune responses including antibody production, cell destruction, and initiation of regulatory mechanisms. In vivo, peptide loading and formation of stable MHC II/peptide complexes is catalyzed by the MHC II like protein HLA-DM (DM). In vitro, CLIP dissociation from HLA DR αβ dimers occurs at different rates depending on the HLA allele, and is facilitated by low pH and by detergents containing 8-10 carbon unbranched hydrocarbons, or by primary aliphatic amines or carboxylic acids.

Of interest to the present invention is the disclosure of Chen et al. J. Exp. Med. Vol. 195, No. 8 pp. 1053-1062 (2002) which shows the presence of CLIP on normal B lymphocytes. See also, Butler et al. Intl. Immunology, Vol. 22, No. 11 pp. 863-873 (2010) which discloses the transfection of the invariant chain to the K562 human erythroleukemic cell line which does not otherwise express the invariant chain.

There remains a need in the art for improved methods of HLA antibody identification for HLA Class II antigens.

SUMMARY

The present invention is related to the observation that Class II antigens produced from recombinant hosts have peptide binding grooves which are filled with peptides from the host and that there is a subset of antigens that do not have a peptide in the peptide binding groove if the host does not express the invariant chain. The CLIP peptide would occupy the peptide binding groove of those Class II antigens if the antigens were expressed in cells that express the invariant chain along with those Class II antigens that bind other endogenous peptides. Chen et al. J. Exp. Med. Vol. 195, No. 8 pp. 1053-1062 (2002)

It is apparently the case that some naturally occurring antibodies will recognize the epitopes exposed in the empty groove. It is further the case that CLIP can be added to those Class II antigens containing a fraction of empty groove antigens to occupy the empty groove and prevent exposure of those epitopes and false positive reactions to antibodies specific to the alternative epitopes. In addition, there are some anti-HLA Class II antibodies specific for particular HLA Class II antigens in which a CLIP peptide is present in the peptide binding groove which will not bind with the same HLA Class II antigen in which a CLIP peptide is absent from the peptide binding groove thus generating false negative reactions. Conversely, there are also antibodies that will not specifically bind to particular HLA Class II antigens in which the CLIP peptide is present but which will bind to the same HLA Class II antigen in which the CLIP peptide is absent.

Further, when HLA Class II antigens are expressed in host cells that do not express the invariant chain the peptide binding groove can be partially filled with other non-CLIP peptides from the host cell. As a consequence, solid phase HLA Class II antigen assays in which the CLIP peptide is absent from the peptide binding groove may yield either a false negative and/or false positive results when compared to cell-based assays in which cells expressed CD74 to accommodate HLA Class II synthesis. Accordingly, providing CLIP to fill the empty groove of HLA Class II antigens that otherwise lack CLIP in their peptide groove can eliminate false positive and fall negative reactions.

Accordingly, solid phase assays are implemented in which HLA Class II antigens have either a CLIP peptide present in or absent from the peptide binding groove wherein "absent from" can be defined as HLA Class II antigens in which the peptide binding groove is free of CLIP peptide above a detectable threshold. Such detectable thresholds can be selected so as to avoid a false positive reaction.

This present invention is directed to the reduction or elimination of false reactivity by providing HLA Class II SABs which include a CLIP peptide in their peptide binding groove. According to one aspect of the invention, HLA Class II SABs are provided with HLA Class II antigens in which a CLIP peptide is present in the peptide binding groove. According to an alternative aspect of the invention HLA Class II SABs are provided in which HLA Class II antigens a CLIP peptide is present in the peptide binding groove along with SABs having HLA Class II antigens in which the peptide binding groove is free of CLIP peptide above a detectable threshold.

According to a further aspect of the invention, the Ii and CLIP are incorporated into the SAB Class II assay manufacturing process, thus improving the accuracy of SAB Class II assays in HLA antibody detection. The Ii and CLIP can be introduced via in vivo or in vitro methods or by selecting hosts having the endogenous Ii chain expression. Alternatively, host cells can be transformed with genes encoding expression of Ii polypeptide which can be co-expressed with genes expressing the HLA Class II antigen. In addition, methods of preparing an HLA Class II antigen in which a CLIP peptide is present in the peptide binding groove above a selected threshold for determination of antibodies specific for HLA Class II antigens in which a CLIP peptide is present in the peptide binding groove are provided comprising transfecting a host cell which expresses the invariant chain with a gene expressing an HLA Class II antigen.

Further, HLA Class II antigens lacking CLIP peptides in their peptide binding grooves above a selected detectable level either as a consequence of their preparation or because of dissociation of the CLIP peptides previously present can be loaded with such CLIP peptides by incubation with an excess of CLIP peptides under conditions selected such that the CLIP will be present in the peptide binding groove of the HLA Class II antigens. The HLA Class II antigens can be incubated in a suitable buffer solution containing CLIP peptide at a concentration of from 5 to 500 μm More preferably the CLIP peptide is present at a concentration of from 10 to 100 μm with a concentration of 50 μm being most preferred. The antigen and CLIP peptide are preferably incubated for two hours at a temperature of 37° C. but those of ordinary skill in the art would appreciate that the incubation could be carried out at higher or lower temperatures ranging from about 4° C. to about 40° C. with lower temperatures and CLIP concentrations requiring longer incubation times to load the CLIP peptide and higher temperatures and CLIP concentrations requiring less time. Further, methods are provided by which HLA Class II antigens with CLIP peptides present in their peptide binding grooves are stored in the presence of CLIP peptides under such conditions selected such that the peptide binding grooves of the HLA Class II antigens will maintain the presence of CLIP peptides.

Specifically provided are methods of preparing an HLA Class II antigen in which a CLIP peptide is present in the peptide binding groove comprising: transfecting a host cell with a gene encoding the invariant chain and expressing said HLA Class II antigen. According to a preferred aspect of the invention the gene encoding the invariant chain is CD74. CD74 has sequence ID P04233 in UNIPROT.

Also provided are methods of preparing an HLA Class II antigen in which a CLIP peptide is present in the peptide binding groove comprising: preparing an HLA Class II antigen and incubating said antigen with CLIP peptide under conditions selected to introduce said CLIP peptide into the antigen peptide binding groove as described above.

Methods of storing an HLA Class II antigen in a buffer containing CLIP peptide are also provided as described above.

Methods are provided for screening for antibodies that specifically bind an HLA Class II antigen in which a CLIP peptide is present in the peptide binding comprising the steps of: preparing a panel comprising a solid-phase substrate having an HLA Class II antigen in which a CLIP peptide is present in the peptide binding groove immobilized or attached hereto; obtaining a serum sample from a human subject, contacting the panel with the serum sample, and detecting binding of antibodies in said serum sample to the HLA Class II antigen in which a CLIP peptide is present in the peptide binding groove. According to these methods the HLA Class II antigen in which a CLIP peptide is present in the peptide binding groove can be prepared by the method of transfecting a host cell with a gene encoding the invariant chain and expressing said HLA Class II antigen, by prepared by the method of transfecting a host cell which expresses the invariant chain with a gene expressing an HLA Class II antigen, by the method of preparing an HLA Class II antigen and incubating said antigen with CLIP peptide under conditions selected to introduce said CLIP peptide into the antigen peptide binding groove or by other methods as would be appreciated by those of skill in the art in light of the teachings herein. It should be noted that such antigens may have non-CLIP peptides present in their peptide binding grooves also.

According to an alternative aspect of the invention such a method can be carried out in which a second solid-phase substrate is provided having an HLA Class II antigen having a peptide binding groove which is free of CLIP peptide above a selected level and wherein antibodies in said serum sample which bind to the HLA Class II antigen in which the peptide binding groove is free of CLIP peptide above a selected level are detected. It should be noted that such antigens may have non-CLIP peptides present in their peptide binding grooves.

Such methods and those described hereafter can be performed wherein the solid-phase substrates are ELISA plates, other solid phase chips and the like including microparticles. According to one preferred aspect of the invention each microparticle presents at least one selected HLA antigen. Further, the methods can be performed wherein binding of an antibody is detected using flow cytometry.

The methods and those described hereafter can also be performed wherein antibody binding is detected with a secondary antibody, preferably wherein the secondary antibody comprises a label selected from the group consisting of a radioactive label, fluorescent label, enzymatic label, colorimetric label avidin label and biotin label.

Such methods and those described hereafter can be performed wherein the human subject is a transplant or transfusion recipient or wherein the human subject is a transplant or transfusion donor.

Also provided are kits for immunologic screening such as kits for screening for antibodies that specifically bind to a selected HLA Class II antigen in which a CLIP peptide is present in the peptide binding groove comprising a panel of solid-phase substrates wherein the panel comprises a solid phase substrate having an HLA Class II antigen in which a CLIP peptide is present immobilized or attached thereto. According to one embodiment the solid-phase substrate is a set of microparticles wherein each microparticle presents at least one HLA antigen. According to an alternative embodiment a second solid phase substrate is provided having said HLA Class II antigen, in which the peptide binding groove is free of CLIP peptide above a selected detectable threshold such as selected to avoid a false positive reaction, immobilized or attached thereto.

Also provided are methods of screening for antibodies that specifically bind an HLA Class II antigen comprising the steps of obtaining a serum sample from a human subject, providing a first solid phase substrate having immobilized or attached thereon said HLA Class II antigen in which a CLIP peptide is present in the peptide binding groove, binding antibodies that specifically bind said HLA Class II antigen in which a CLIP peptide is present in the peptide binding groove to form an antibody/antigen complex, separating the antibody/antigen complex from the serum sample to generate a serum sample essentially free of antibodies that specifically bind said HLA Class II antigen in which a CLIP peptide is present in the peptide binding groove, contacting the serum sample that is essentially free of antibodies that specifically bind said HLA Class II antigen in which a CLIP peptide is present in the peptide binding groove with a second solid-phase substrate having said HLA Class II antigen having a peptide binding groove which is free of CLIP peptide above a selected level immobilized or attached thereto, and detecting binding of an antibody in said serum sample that is essentially free of antibodies that specifically bind said HLA Class II antigen in which a CLIP peptide is present in the peptide binding groove to the HLA Class II antigen having a peptide binding groove which is free of CLIP peptide above a selected level in order to identify the potential presence of antibodies which are specific for said HLA Class II having a peptide binding groove which is free of CLIP peptide above a selected level. According to one preferred aspect the solid-phase substrates are microparticles, wherein each microparticle presents at least one selected HLA antigen.

Also provided are methods of screening for antibodies that specifically bind an HLA Class II antigen comprising the steps of: obtaining a serum sample from a human subject, providing a first solid phase substrate having immobilized or attached thereon said HLA Class II antigen in which the peptide binding groove is free of CLIP peptide above a selected detectable threshold as might be selected to avoid a false positive reaction; binding antibodies that specifically bind said HLA Class II antigen having a peptide binding groove which is free of CLIP peptide above a selected level to form an antibody/antigen complex, separating the antibody/antigen complex from the serum sample to generate a serum sample essentially free of antibodies that specifically bind said HLA Class II antigen in which the peptide binding groove is free of CLIP peptide above a selected detectable threshold; contacting the serum sample that is essentially free of antibodies that specifically bind said HLA Class II antigen having a peptide binding groove which is free of CLIP peptide above a selected level with a second solid-phase substrate having said HLA Class II antigen in which a CLIP peptide is present in said peptide binding groove immobilized or attached thereto, and detecting binding of an antibody in said serum sample that is essentially free of antibodies that specifically bind said HLA Class II antigen in which the peptide binding groove is free of CLIP peptide above a selected detectable threshold to the HLA Class II antigen in which a CLIP peptide is present in the peptide binding groove in order to identify the potential presence of antibodies which are specific for said HLA Class II antigen in which a CLIP peptide is present in the peptide binding groove.

Also provided are methods of screening comprising the steps of: contacting a cell that presents an HLA Class II antigen having a peptide binding groove which is free of CLIP peptide above a selected level with a serum sample comprising antibodies that specifically bind said HLA Class II antigen in which the peptide binding groove is free of CLIP peptide above a selected detectable threshold to form an antibody/antigen complex, separating the antibody/antigen complex from the serum sample to generate a serum sample essentially free of antibodies that specifically bind said HLA Class II antigen having a peptide binding groove which is free of CLIP peptide above a selected level, contacting the serum sample that is essentially free of antibodies that specifically bind to said HLA Class II antigen having a peptide binding groove which is free of CLIP peptide above a selected level with a solid phase substrate having immobilized thereon or attached thereto HLA Class II antigen in which a CLIP peptide is present in the peptide binding groove, and detecting binding of an antibody in said serum sample that is essentially free of antibodies that specifically bind to said HLA Class II antigen in which the peptide binding groove is free of CLIP peptide above a selected threshold to the HLA Class II antigen to the solid-phase substrate in order to identify the presence of antibodies specific for said HLA Class II antigen in which a CLIP peptide is present in the peptide binding groove.

Methods of screening are provided which comprise the steps of: contacting a cell that presents an HLA Class II antigen in which a CLIP peptide is present in the peptide binding groove with a serum sample comprising antibodies that specifically bind said HLA Class II antigen in which CLIP peptide is present, separating the antibody/antigen complex from the serum sample to generate a serum sample essentially free of antibodies that specifically bind said HLA Class II antigen in which a CLIP peptide is present in the peptide binding groove, contacting the serum sample that is essentially free of antibodies that specifically bind to said HLA Class II antigen in which a CLIP peptide is present in the peptide binding groove with a solid phase substrate having immobilized thereon or attached thereto HLA Class II antigen in which the peptide binding groove is free of CLIP peptide above a selected threshold and detecting binding of an antibody in said serum sample that is essentially free of antibodies that specifically bind to said HLA Class II antigen in which a CLIP peptide is present in the peptide binding groove to the HLA Class II antigen to the solid-phase substrate in order to identify the presence of antibodies specific for said HLA Class II antigen in which the peptide binding groove is free of CLIP peptide above a selected threshold.

Compositions of matter are provided comprising a solid phase substrate having an HLA Class II antigen immobilized thereto and a buffer containing an excess of CLIP peptide. One preferred composition is that in which the solid phase substrate is a single antigen bead ("SAB").

DETAILED DESCRIPTION

The present invention relates to compositions and methods for reducing false negative and false positive results by providing HLA Class II antigens in which CLIP peptides are present in the peptide binding groove as well as HLA Class II antigens having a peptide binding groove which is free of CLIP peptide above a selected level.

HLA Class II antigens and solid phase assay kits can be prepared and practiced by methods known to the art. Incorporated by reference herein are the disclosures of U.S. Pat. No. 9,354,238 for Compositions and methods for the detection of antibodies to native human leukocyte antigen and U.S. Pat. No. 9,250,247 for Methods of detecting antibodies specific for denatured HLA antigens.

Preparation of HLA Antigens

In some embodiments, the HLA antigen is a fusion protein, but it need not be. For example, the invention provides for transforming or transfecting host cells with a nucleic acid encoding the amino acid sequence of an HLA antigen polypeptide fused with a heterologous domain selected from the group consisting of B2 signal peptide, HLA cytoplasmic domain, EK Tag, V5 Tag or DPD Tag.

A nucleic acid molecule encoding the amino acid sequence of an HLA antigen polypeptide may be fused with the domain and inserted into an appropriate expression vector using standard ligation techniques. Exemplary vectors include, but are not limited to, bacterial vectors, eukaryotic vectors, plasmids, cosmids, viral vectors, adenovirus vectors and adenovirus associated vectors.

The HLA antigen polypeptide may contain a sequence encoding a "tag" or exogenous amino acid sequence, such as an oligonucleotide molecule located at the 5' or 3' end of the HLA polypeptide coding sequence; an oligonucleotide sequence encoding polyHis (such as hexaHis), (SEQ ID NO: 3)), FLAG, hemaglutinin influenza virus (HA), V5 or myc or other tags, for which commercially available antibodies exist. This tag may be fused to the HLA polypeptide upon expression. The term "exogenous" as used herein refers to a substance or molecule originating or produced outside of an organism. The term "exogenous gene" or "exogenous nucleic acid molecule," as used herein, refers to a nucleic acid that codes for the expression of RNA and/or protein that has been introduced ("transformed") into a cell or a progenitor of the cell. An exogenous gene may be from a different species (and so a "heterologous" gene) or from the same species (and so a "homologous" gene), relative to the cell being transformed.

In some embodiments, the expression vectors contain sequences for cloning and expression of exogenous nucleotide sequences. Such sequences may include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element.

In some embodiments, the vector comprises a selectable marker gene element. A selectable marker gene element encoding a protein necessary for the survival and growth of a host cell grown in a selective culture medium may also be a component of the expression vector. Exemplary selection marker genes include those that encode proteins that complement auxotrophic deficiencies of the cell; or supply critical nutrients not available from complex media. The invention also contemplates that the HLA antigen polypeptides described herein comprise one or more of these exogenous amino acid sequences.

In some embodiments, a leader, or signal, sequence is used to direct HLA antigen polypeptide out of the stem cell after administration. For example, a nucleotide sequence encoding the signal sequence is positioned in the coding region of the HLA antigen encoding nucleic acid or directly at the 5' end of the HLA antigen coding. The signal sequence may be homologous or heterologous to the HLA antigen polypeptide gene or cDNA, or chemically synthesized. The secretion of the HLA antigen polypeptide from the stem cell via the presence of a signal peptide may result in the removal of the signal peptide from the secreted HLA antigen polypeptide. The signal sequence may be a component of the vector, or it may be a part of the nucleic acid molecule encoding the HLA antigen polypeptide that is inserted into the vector.

In some embodiments, the domain is a cytoplasmic domain, or traffic signal, sequence. Cytoplasmic domain sequences may be used to direct the HLA antigen polypeptides out of the cells after administration or to modify its characteristics to avoid cell signaling pathway that leads to cell death.

The vectors described herein optionally comprise a promoter operably linked to the nucleic acid encoding the HLA antigen polypeptide. Promoters are untranscribed sequences located upstream to the start codon of a structural gene that control the transcription of the structural gene. Inducible promoters initiate increased levels of transcription from DNA under their control in response to some change in culture conditions, such as the presence or absence of a nutrient or a change in temperature. Alternatively, constitutive promoters initiate continual gene product production with little or no control over gene expression. A large number of promoters, recognized by a variety of potential host cells, are well known. The native HLA gene promoter sequence may be used to direct amplification and/or expression of the HLA polypeptide nucleic acid molecule. A heterologous promoter also may be used to induce greater transcription and higher yields of the HLA polypeptide expression as compared to the HLA polypeptide expression induced by the native promoter.

In addition, an enhancer sequence may be inserted into the vector to increase the transcription of a DNA encoding the HLA antigen polypeptide. Enhancers are cis-acting elements of DNA, usually about 10-300 bp in length, that act on the promoter to increase transcription. Enhancer sequences available from mammalian genes include globin, elastase, albumin, alpha-feto-protein and insulin. Exemplary viral enhancers that activate eukaryotic promoters include the SV40 enhancer, the cytomegalovirus early promoter enhancer, the polyoma enhancer, and adenovirus enhancers. While an enhancer may be spliced into the vector at a position 5' or 3' to a nucleic acid molecule encoding the HLA antigen polypeptide, it is typically located at a site 5' from the promoter. The enhancer may be native to the HLA antigen polynucleotide sequence or may be heterologous to the HLA antigen polynucleotide sequence.

The transformation of an expression vector encoding an HLA antigen polypeptide into a host cell may be accomplished by well-known methods such as transfection, infection, calcium chloride, electroporation, microinjection, lipofection or the DEAE-dextran method or any other technique known in the art. These methods and other suitable methods are well known in the art, for example, in Sambrook, Molecular Cloning: A Laboratory Manual, Cold Spring Harbor Laboratory Press; 3rd ed., 2001, the disclosure of which is incorporated herein by reference in its entirety.

Expression vectors of the invention may be constructed from a starting vector such as a commercially available vector. Such vectors may or may not contain all of the desired flanking sequences. Where one or more of the desired flanking sequences are not already present in the vector, they may be individually obtained and ligated into the vector. Methods used for obtaining each of the flanking sequences are well known to one skilled in the art.

Preferred vectors for practicing this invention are those which are compatible with bacterial, insect, and mammalian host cells. Such vectors include, inter alia, pCRII, pCR3, and pcDNA3.1 (Invitrogen Company, Carlsbad, CA), pBSII (Stratagene Company, La Jolla, CA), pET15? (Novagen, Madison, WI), pGEX (Pharmacia Biotech, Piscataway, NJ), pEGFP-N2 (Clontech, Palo Alto, CA), pETL (BlueBacII; Invitrogen), pDSR-alpha (PCT Publication No. WO90/14363) and pFastBacDual (Gibco/BRL, Grand Island, NY).

Additional suitable vectors include, but are not limited to, cosmids, plasmids or modified viruses, but it will be appreciated that the vector system must be compatible with the selected host cell. Such vectors include, but are not limited to plasmids such as Bluescript® plasmid derivatives (a high copy number ColE1-based phagemid, Stratagene Cloning Systems Inc., La Jolla CA), PCR cloning plasmids designed for cloning Taq-amplified PCR products (e.g., TOPO™ TA Cloning® Kit, PCR2.1® plasmid derivatives, Invitrogen, Carlsbad, CA), and mammalian, yeast, or virus vectors such as a baculovirus expression system (pBacPAK plasmid derivatives, Clontech, Palo Alto, CA). The recombinant molecules can be introduced into host cells via transformation, transfection, infection, or other known techniques.

Host cells may be prokaryotic host cells (such as *E. coli*) or eukaryotic host cells (such as a yeast cell, an insect cell or a vertebrate cell). The host cell, when cultured under appropriate conditions, synthesizes a non-HLA antigen polypeptide (or HLA antigen polypeptide) described herein which can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity, such as glycosylation or phosphorylation, and ease of folding into a biologically active molecule.

A number of suitable host cells are known in the art and many are available from the American Type Culture Collection (ATCC), 10801 University Boulevard, Manassas, VA 20110-2209. Examples include, but are not limited to, mammalian cells, such as Chinese hamster ovary cells (CHO) (ATCC No. CCL61) CHO DHFR-cells (Urlaub et al., Proc. Natl. Acad. Sci. USA, 97:4216-4220 (1980)), human embryonic kidney (HEK) 293 or 293T cells (ATCC No. CRL1573), Hmy2.C1R cells (ATCC No. CRL1992) or K562 cells (ATCC No. CCL243). The selection of suitable mammalian host cells and methods for transformation, culture, amplification, screening and product production and purification are known in the art. Other suitable mammalian cell lines are the monkey COS-1 (ATCC No. CRL1650) and COS-7 cell lines (ATCC No. CRL1651), and the CV-1 cell line (ATCC No. CCL70). Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, mouse neuroblastoma N2A cells, HeLa, mouse L-929 cells, 3T3 lines derived from Swiss, Balb-c or NIH mice, BHK or HaK hamster cell lines, which are available from the ATCC. Each of these cell lines is known by and available to those skilled in the art of protein expression.

Methods of Detecting HLA Antibodies

The invention provides methods of detecting antibodies specific for HLA Class II antigens in which a CLIP peptide is present in the peptide binding groove, antibodies specific for HLA Class II antigens having a peptide binding groove which is free of CLIP peptide above a selected level and antibodies specific for HLA Class II antigens with and without a CLIP peptide present in the peptide binding groove in a biological sample. The methods are carried out with solid-phase panels wherein the panel comprises substrates that present (or have immobilized thereon) at least one or more selected HLA Class II antigens in which a CLIP peptide is present in the peptide binding groove, and substrates that present (or have immobilized thereon) at least one or more selected HLA Class II having a peptide binding groove which is free of CLIP peptide above a selected level. Preferably the HLA antigens are presented on microbeads.

Exemplary solid-phase assays such as assays of the invention may use solid substrates such as microparticles, magnetic particles such as ferromagnetic beads and paramagnetic beads, microtiter plates, membranes, filters, glass, metal, metal-alloy, anopol, polymers, nylon, plastic or microarrays such as protein chips. Microarrays may be of any material such as glass or silica. Binding on a microtiter plate may be detected using ELISA assays, RIA assays or other immunosorbent sandwich assays. Binding on a filter may be detected using immunoblotting techniques.

The solid-phase assays of the invention may be carried out with microparticles, microbeads, magnetic beads, beads or microspheres of any material, e.g. silica, gold, latex, polymers such as polystyrene, polysulfone and polyethyl, or hydrogel. Additional exemplary microparticles are encoded with the dyes and the antigens are immobilized to the encoded microparticles. The microparticles used in the methods of the invention are commercially available from sources such from Luminex Inc., Invitrogen (Carlsbad, CA), Polysciences Inc. (Warrington, PA) and Bangs Laboratories (Fishers, IN) to name a few.

The microparticles of the invention may comprise a detectable label or another identifying characteristic. The microparticles may comprise a single fluorescent dye or multiple fluorescent dyes. In one embodiment, the microparticles are internally labeled with fluorescent dyes and contain surface carboxyl groups for covalent attachment of biomolecules. In another embodiment, the microparticles are internally labeled with fluorescent dyes and contain a surface layer of Avidin for near covalent binding of biotin and biotinylated ligands. In another embodiment, the microparticles may comprise a combination of different dyes, such as a fluorescent and a non-fluorescent dye. For example, the microparticles may be labeled with E)-5-[-[2-methoxycarbonyl)ethenyl]cytidine, which is a nonfluorescent molecule, that when subjected to ultraviolet (UV) irradiation yields a single product, 3-β-D-ribofuranosyl-2, 7-dioxopyrido[2,3-d]pyrimidine, which displays a strong fluorescence signal. In another embodiment, the microparticles may comprise bar codes as an identifiable characteristic as described in U.S. Patent Publication No. US 20070037195.

In another embodiment, the microparticles may be nanocrystals or quantum dots. These nanocrystals are substances that absorb photons of light, then re-emit photons at a different wavelength (fluorophores). In addition, additional florescent labels, or secondary antibodies may be conjugated to the nanocrystals. These nanocrystals are commercially available from sources such as Invitrogen and Evident Technologies (Troy, N.Y.).

The invention can be carried out with any system that detects the identifiable characteristic or label, such as FLOW cytometry. Detection of fluorescent labels may also be carried out using a microscope or camera that will read the image on the microparticles, such as the Bioarray BeadChip (Bioarray Solutions, Ltd., Warren, N.J.). The BeadChip format combines microparticle ("bead") chemistry with semiconductor wafer processing in which binding to the microparticle is recorded using an optical microscope and camera.

The invention also may be carried out using column chromatography, affinity chromatography, thin layer chromatography, liquid-phase immunodiagnostic (LIPA) assays, liquid-phase chemiluminescent ELISA and liquid-phase immunoradiometric (IRMA) to name a few.

Biological samples includes whole blood, blood derivatives, red blood cell concentrates, plasma, serum, fresh frozen plasma, whole blood derived platelet concentrates, apheresis platelets, pooled platelets, intravenous gammaglobulin, cryoprecipitate, cerebrospinal fluid, tissues and cells such as epithelial cells, such as those collected from the bucal cavity, stem cells, leukocytes, neutrophils and granulocytes. The biological samples may be obtained from a human donor of tissue or cells intended for transplantation or a human donor of blood or blood derivatives intended for transfusion. The biological sample may be obtained from a healthy bone marrow donor or a subject of a paternity test. The biological sample may also be obtained from a human subject that is an intended recipient of a transplant or transfusion, or the human subject that is donating the tissue or organ intended for transplantation or transfusion. Alternatively, the biological sample may be obtained directly from tissues or cells that are intended for transplantation in a human recipient. In addition, the biological sample may be obtained from blood or blood derivatives that are intended for transfusion in a human recipient.

The antibodies of the invention may be polyclonal antibodies, monoclonal antibodies, antibody fragments which retain their ability to bind their unique epitope (e.g., Fv, Fab and F(ab)2 fragments), single chain antibodies and human or humanized antibodies. Antibodies may be generated by techniques standard in the art using an antigenic HLA epitope. See, e.g. Kohler et al., *Nature*, 256:495-497 (1975), Brodeur et al., Monoclonal Antibody Production Techniques and Applications, pp. 51-63 (Marcel Dekker, Inc., New York, 1987). Antibody molecules of the present invention include the classes of IgG (as well as subtypes IgG 1, IgG 2a, and IgG2b), IgM, IgA, IgD, and IgE.

The antibodies of the invention may be labeled for detection of binding within the biological sample. The antibodies may comprise a radioactive label such as $^{3}$H, $^{14}$C, $^{32}$P, $^{35}$S, or $^{125}$I. In addition, the labels may be a fluorescent or chemiluminescent compound, such as fluorescein isothiocyanate, phycoerythrin, rhodamine, or luciferin. The labels may be enzymes such as alkaline phosphatase, β-galactosidase, biotin and avidin or horseradish peroxidase (Bayer et al., Meth. Enz., 184:138-163 (1990)).

The antibodies specific for HLA antigens may be attached to solid substrates such as membranes, beads, filters, glass, silicon, metal, metal-alloy, anopore, polymeric, nylon or plastic for detection of antigens in a biological sample.

Specific binding of an antibody to an HLA antigen within a biological sample may be carried out using Western blot analysis with immunoblotting, immunocytochemistry, immunohistochemistry, dot blot analysis, flow cytometry, ELISA assays or RIA assays. These techniques and other approaches are conventional in the art (See Sambrook et al., Molecular Cloning: A Laboratory Manual, cold Springs Harbor Laboratories (New York, 1989).

Of interest to the present invention are assay methods making use of flow cytometry. Wilson et al., J. Immunol. Methods 107: 231-237 (1988) disclose the use of polyacrylamide microspheres coupled with cell membrane proteins in immunofluorescence assays for antibodies to membrane-associated antigens. The method is said to make possible the rapid flow cytometric analysis of plasma membrane antigens from cell populations that would otherwise be unsuitable for use in flow cytometry. Scillian et al., Blood 73: 2041-2048 (1989) disclose the use of immunoreactive beads in flow cytometric assays for detection of antibodies to HIV. Frengen et al., Clin. Chem. 40/3: 420-425 (1994) disclose the use of flow cytometry for particle-based immunoassays of cefetoprotein (AFP). This reference further reports the ability of serum factors to cross-link labeled mouse monoclonal antibodies of irrelevant specificity to different particle types coated with various immunoglobulins.

Flow cytometry methods using lymphocytes are also known but suffer with difficulties because of the activity of auto-antibodies. See Shroyer et al., Transplantation 59:626-630 Moreover, when using flow cytometry with lymphocytes, use of ten or more different lymphocytes tends to result in confusing signals. As a consequence, studies using lymphocytes have been limited by presenting a small panel of HLA antigens that do not effectively simulate the distribution of HLA antigens in a normal human population.

Sumitran-Karuppan et al., Transplantation 61: 1539-1545 (1996) discloses the use of magnetic beads which use an anti-HLA capture antibody to immobilize a variety of soluble HLA antigens pooled from 80 to 100 individuals on each bead. The beads can then be directly added to patient serum for efficient absorption of HLA antibodies. The reference discloses visualization of antibody binding to the antigen-coated beads using flow cytometry. The reference suggests that this development will allow testing for antibody specificity for crossmatching purposes and for the screening of panel-reactive antibodies. The methods of Sumitran-Karuppan are limited, however, because the pooling of antigens causes sensitivity to certain rare HLA antigens. Moreover, the method is not capable of detecting the percentage of PRA.

The invention also provides for kits to carry out the methods of the invention. In particular, the invention provides for kit for determining the presence of antibodies in serum of a subject against HLA Class II antigens comprising a first collection of solid-phase substrates wherein each solid-phase substrate is coated with different purified HLA antigens to represent the HLA antigen population of a single cell line such that said collection simulates the distribution of HLA antigens in a normal human. The antigens provided in the kit may be conjugated to solid substrates in the kit. Alternatively, the kit comprises solid substrates and antigens and the skilled artisan can conjugate the antigens to the solid substrates allowing for optimization of the antigens used in the assay. The kits may also comprise the reagents necessary to detect and measure antibodies, such as HLA antibodies for use as a positive control.

The HLA antigens comprise Class II HLA antigens (e.g., wherein the HLA antigens are selected such that the HLA antigens presented on the solid phase substrate comprise Class II HLA antigens so as to simulate the distribution of Class II HLA antigens in a normal human population). In some embodiments, the HLA antigens also comprise HLA Class 1 antigens.

The kits useful herein may further comprise any components necessary to carry out the detection assays that are conventional in the art. For example, the kits may comprise buffers, loading dyes, gels such as polyacrylamide gels and molecular weight markers for preparing SDS-PAGE gels to carry out Western blots. The kits may also comprise filters, membranes blocking buffers, control buffers, isotype control antibodies, wash buffers or buffers and reagents for detection to carry out immunoblotting or dot blotting analysis such as labeled secondary antibodies. The kit may also comprise fixing reagents, blocking buffers, control buffers, wash buffers, staining dyes and detection reagents including anti-idiospecific antibodies. Furthermore, the kits may comprise the necessary reagents and tools to carryout flow cytometry, ELISA assays, RIA assays or microtoxicity assays.

In some embodiments, the detecting step comprises detecting labeled ligand bound to the complex to determine the presence or absence of antibodies reactive against selected HLA Class II antigens. In some embodiments, detecting of the labeled ligand is carried out by flow cytometry. In some embodiments, the detecting step comprises detecting the presence of the complex using a solid phase immunoassay or a multiplexed bead immunoassay.

The solid-phase substrate can be any solid substrate known in the art. In some embodiments, the solid-phase substrate is selected from the group consisting of micropartical, microbead, magnetic bead, ion torrent bead, flow cytometer bead and an affinity purification column. In some embodiments, the solid-phase substrate is a microbead. In some embodiments, the microbead is a latex microbead. The microbead, in some embodiments, has a diameter ranging from about 2 μm to about 15 μm, inclusive. Microbeads having a diameter of about 2 μm, 3 μm, 4 μm, 5 μm, 6 μm, 7 μm, 8 μm, 9 μm, 10 μm, 11 μm, 12 μm, 13 μm, 14 μm or 15 μm are also contemplated. In some embodiments, at least one microbead presenting Class I HLA antigens is 3 μm is diameter. In some embodiments, at least one microbead presented Class II HLA antigens is 5 μm in diameter. In some embodiments, the microbeads comprise a mixture of 3 μm microbeads presenting Class I HLA antigens and 5 μm microbeads presented Class II HLA antigens.

In some embodiments, each solid phase substrate is detectably distinguishable from other solid phase substrates within the composition. In some embodiments, the detectably distinguishable solid phase substrates are distinguishable by fluorescent labels.

The HLA Class II antigens can be incubated in a suitable buffer solution containing CLIP peptide at a concentration of from 5 to 500 μm. More preferably the CLIP peptide is present at a concentration of from 10 to 100 µm with a concentration of 50 µm being most preferred. The antigen and CLIP peptide are preferably incubated for two hours at a temperature of 37° C. but those of ordinary skill in the art would appreciate that the incubation could be carried out at higher or lower temperatures ranging from about 4° C. to about 40° C. with lower temperatures and CLIP concentrations requiring longer incubation times to load the CLIP peptide and higher temperatures and CLIP concentrations requiring less time. In addition the HLA Class II antigens can be kept stored under the conditions described above.

Peptides useful for practice of the present invention comprise the core sequence of the CLIP peptide including MRMATPLLM (SEQ ID NO: 1) but can be shorter or longer in a range of 15-30 amino acids. According to one aspect of the invention CLIP peptide 81-105, KPVSQMRMATPLLMRPM (SEQ ID NO: 2) can be used.

The CLIP peptide can be chemically synthesized or can be introduced via CD74 recombinant via natural processing in a recombinant host. CD74 has sequence ID P04233 in UNIPROT. CLIP peptides can be lyophilized and can be reconstituted in water or in solutions such as 1×PBS as is within the ordinary skill of those in the peptide art. It is preferably stored at −20° C. in order to avoid proteolysis.

Other aspects and advantages of the present invention will be understood upon consideration of the following illustrative examples.

Example 1

According to this example, two different recombinant host cell lines were evaluated to determine expression of the invariant chain.

Figure 1:
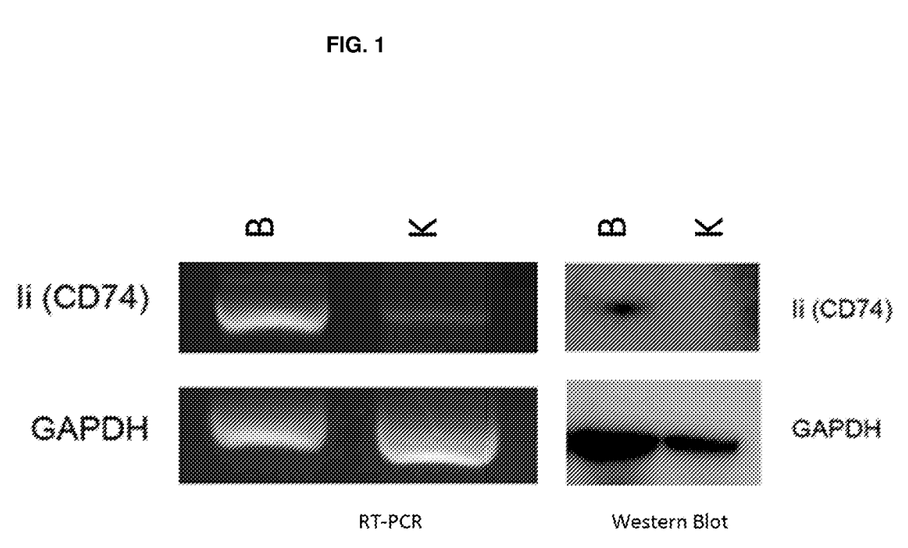
FIG. 1 depicts the RT-PCR and Western blot of the expression levels of the invariant chain in the recombinant hosts, B and K lines.

The results presented in FIG. 1 show that although mRNA of invariant chain can be detected in recombinant cell line host "K" (i.e., K562 cell line), the amount of invariant chain is very limited and is not detected by the Western Blot analysis. On the other hand, recombinant cell line host "B" (BLS cell line) has abundant invariant chain that can be detected by both RT-PCR and Western blot. Thus, if expression of invariant chain and the presence of CLIP peptide in the peptide binding groove of a recombinantly produced HLA Class II antigen is desired it is important that a host cell line capable of expressing the invariant chain peptide be used.

Example 2

According to this example, a single antigen bead presenting an HLA Class II antigen in which CLIP peptide is absent from the peptide binding groove is incubated with CLIP peptide under conditions selected to introduce the CLIP peptide into the antigen peptide binding groove.

Specifically, peptide was loaded onto HLA beads according to the method wherein LABScreen™ (Luminex®) multiplexing assay beads coated with HLA specific Class II antigens were used and treated with 0.05M citrate phosphate buffer, pH5.5 (CPB, Sigma Aldrich) for 1 hour at 37 C to release pre-bound peptides from the MHC (un-loading). This treatment is akin to the cell's endogenous endosomal pH environment where the peptide loading occurs. The treatment has been shown not to compromise the MHC structural conformation on the beads. Biotinylated-CLIP peptide loading was performed in 100 µl volume in CPB at pH7.2 with 1 mM PefaBloc® inhibitor (Sigma Aldrich) for 2 hours at 37 C with no peptide (−ct) or 50 µM final peptide concentration. Experimental samples were washed in 1×PBS and incubated with 100 ul 1× Streptavidin-PE (to detect the presence of the biotinylated CLIP), or 20 µl neat serum (to detect human HLA specific IgGs) or 1 µg of MoAb (to detect specific targeted antigen of interest). Data acquisition was immediately performed on the Luminex® 200™ analyzer.

According to this example single antigen beads labeled with DRB5*01:01 HLA Class II antigen expressed in a K cell line host (which expresses low levels of the invariant chain as described in Example 1) and lacking the presence of a CLIP peptide in the peptide binding groove fails to detect the positive human sera designated EM and HG.

After incubation of the antigen beads in the presence of CLIP protein the HLA Class II antigen beads having CLIP protein present in the peptide binding groove were tested for reaction to anti-HLA Class II antibodies. A non-reactive antigen, DRB1*03:01 served as the control to confirm that both positive sera, EM and HG, require DRB5*01:01 loaded with CLIP in order to show the reactivity. Table 1 presents the reaction pattern of EH and HG sera in assays for DRB5*01:01 and DRB1*03:01 antigens loaded with CLIP peptides.

TABLE 1

The reaction pattern of sera EH and HG on the SAB assays with Data are presented as median florescent intensity (MFI).

|  | DRB5*01:01 | | DRB1*03:01 | |
| --- | --- | --- | --- | --- |
|  | Control | CLIP Loaded | Control | CLIP Loaded |
| Negative Control (LSNC) | 308 | 414 | 265 | 316 |
| Positive Control (FJ) | 22915 | 22405 | 23721 | 23332 |
| EM Sera | 1173 | 9902 | 281 | 397 |
| HG Sera | 2749 | 10202 | 1053 | 618 |
| Anti-biotinylated CLIP | 840 | 4596 | 296 | 2811 |

These data show that both positive sera, EM and HG require DRB5*01:01 loaded with CLIP in order to show reactivity. Accordingly, without CLIP, DRB5*0101 (control) failed to recognize the positive sera EM and HG indicating that Class II antigen without CLIP gave false negative results.

Example 3

According to this example, an in vivo expression of DRB5*0101 HLA Class II antigen was carried out in the K cell line host with and without co-expression of the invariant chain molecule. Table 2 shows that HLA Class II antigen made from co-expression of the invariant chain molecule and HLA Class II DRB5*01:01 antigen in the K line host reacts to the positive sera, EH and HG, while the antigens from the recombinant DRB5*0101 K line host without expression of the invariant chain molecule cease to react to the positive sera EH and HG.

Specifically, HLA Class II DRB5*0101 are co-transduced with the CD74 (precursor of CLIP) by Lenti expression system to generate recombinant cells.

TABLE 2

The reaction pattern of positive sera EH and HG on the recombinant protein DRB5*0101 generated from K line host co-expression with or without invariant chain protein. Data are presented as median florescent intensity (MFI)

|  | Recombinant DRB5*01:01 | Recombinant DRB5*01:01 co-expression with Ii |
|---|---|---|
| EH Sera | 382 | 19464 |
| HG Sera | 325 | 18993 |
| Anti HLA Class II (PCII) | 22448 | 22434 |
| Anti CLIP | 26 | 10900 |
| Anti CD74 | 788 | 13052 |
| Negative Control (LSNC) | 264 | 190 |

Example 4

According to this example, an in vitro CLIP peptide loading test was carried out. Specifically, peptide was loaded onto HLA beads according to the method wherein LABScreen™ (Luminex®) multiplexing assay beads coated with HLA specific Class II antigens. Biotinylated-CLIP peptide loading was performed in 100 µl volume in CPB at pH7.2 with 1 mM PefaBloc® inhibitor (Sigma Aldrich) for 2 hours at 37 C with no peptide (control) or 50 µM final peptide concentration. Experimental samples were washed in 1×PBS and incubated with 100 ul 1× Streptavidin-PE (to detect the presence of the biotinylated CLIP), or 20 µl neat serum (to detect human HLA specific IgGs) or 1 µg of MoAb (to detect specific targeted antigen of interest). Data acquisition was immediately performed on a Luminex® 200™ analyzer.

Figure 2:
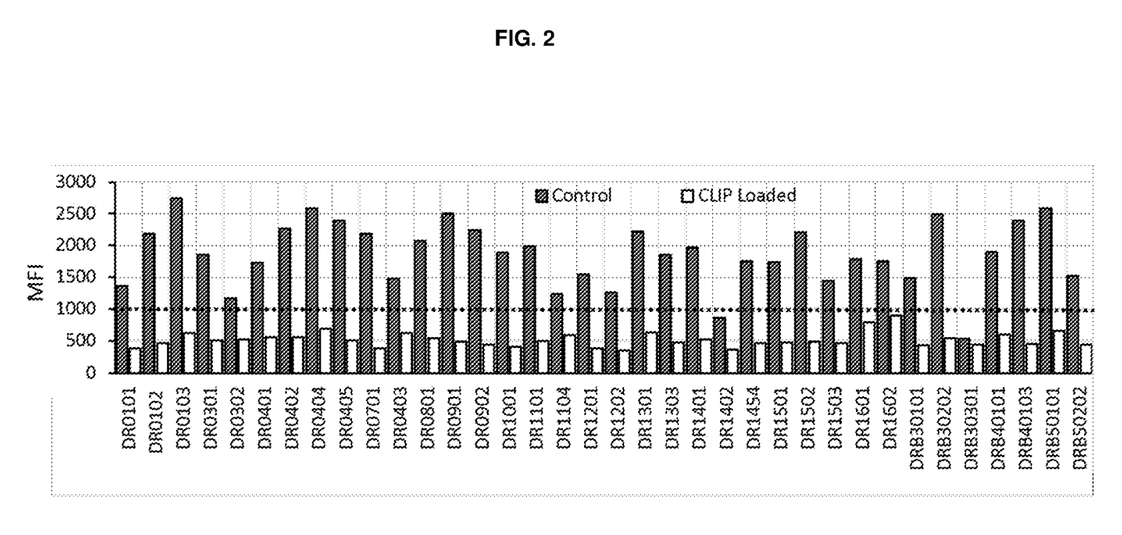
FIG. 2 depicts the reaction pattern of negative sera HS in the SAB assay before and after loading with CLIP peptide.

The results depicted in FIG. 2 show that a negative serum, HS shows false positive reactivity on HLA DR recombinant proteins generated from K line host without invariant chain molecule. Specifically, FIG. 2 depicts reaction pattern of negative sera HS in the SAB assay before and after CLIP loading process with the positive/negative cutoff line at 1000 MFI.

The negative HB sera exhibits broad reactivity to the single antigen bead and gives false positive reactivity. The same negative HS serum ceases to show false positive reactivity after the HLA DR recombinant proteins have been loaded with CLIP peptides as described above. The white bars (loaded with CLIP) and dark grey bars (no CLIP) are compared and show in FIG. 2 with MFI equal to 1000 (dotted line) as the cutoff between positive and negative that adding CLIP clearly eliminates the false positive result of the sera.

Example 5

According to this example, an in vitro process for removal of CLIP peptides from B cell line produced recombinant antigens is carried out according to the method of Yin, et al. Curr. Protoc. Immunol. 106: 5.10.1-5.10.12 (2014). Specifically, LABScreen™ (Luminex®) multiplexing assay beads coated with HLA DRB5*01:01 HLA specific Class II antigens from B line host antigens were used and treated with 0.05M citrate phosphate buffer, pH5.5 (CPB, Sigma Aldrich) for 1 hour at 37 C to release pre-bound CLIP peptides from the MHC. The resulting peptide was evaluated for reactivity to positive sera HG. Table 3 shows the results that partial CLIP removal from the HLA DRB5*01:01 antigens from B line host results in decreased reactivity of positive sera HG.

TABLE 3

The reaction pattern of the HG sera on the recombinant DRB5*01:01 generated from B line host before and after partial CLIP removal. Data are presented as median florescent intensity (MFI).

|  | Control | Partial CLIP Removal |
|---|---|---|
| HG Sera | 7892 | 5397 |
| Anti HLA Class II (FJ) | 23584 | 22853 |
| Negative Control (LSNC) | 607 | 1906 |

Example 6

According to this example, the method of Example 2 is repeated wherein a single antigen bead presenting an HLA Class II antigen in which CLIP peptide is absent from the peptide binding groove was incubated with CLIP peptide under conditions selected to introduce the CLIP peptide into the antigen peptide binding groove.

Specifically, peptide was loaded onto HLA beads according to the method wherein LABScreen™ (Luminex®) multiplexing assay beads coated with HLA specific Class II antigens were used and treated with 0.05M citrate phosphate buffer, pH5.5 (CPB, Sigma Aldrich) for 1 hour at 37 C to release pre-bound peptides from the MHC (un-loading). This treatment is akin to the cell's endogenous endosomal pH environment where the peptide loading occurs. The treatment has been shown not to compromise the MHC structural conformation on the beads. Biotinylated-CLIP peptide loading was performed in 100 µl volume in CPB at pH7.2 with 1 mM PefaBloc® inhibitor (Sigma Aldrich) for 2 hours at 37 C with no peptide (–ct) or 50 µM final peptide concentration. Experimental samples were washed in 1×PBS and incubated with 100 ul 1× Streptavidin-PE (to detect the presence of the biotinylated CLIP), or 20 µl neat serum (to detect human HLA specific IgGs) or 1 µg of MoAb (to detect specific targeted antigen of interest). Data acquisition was immediately performed on the Luminex® 200™ analyzer.

Figure 3:
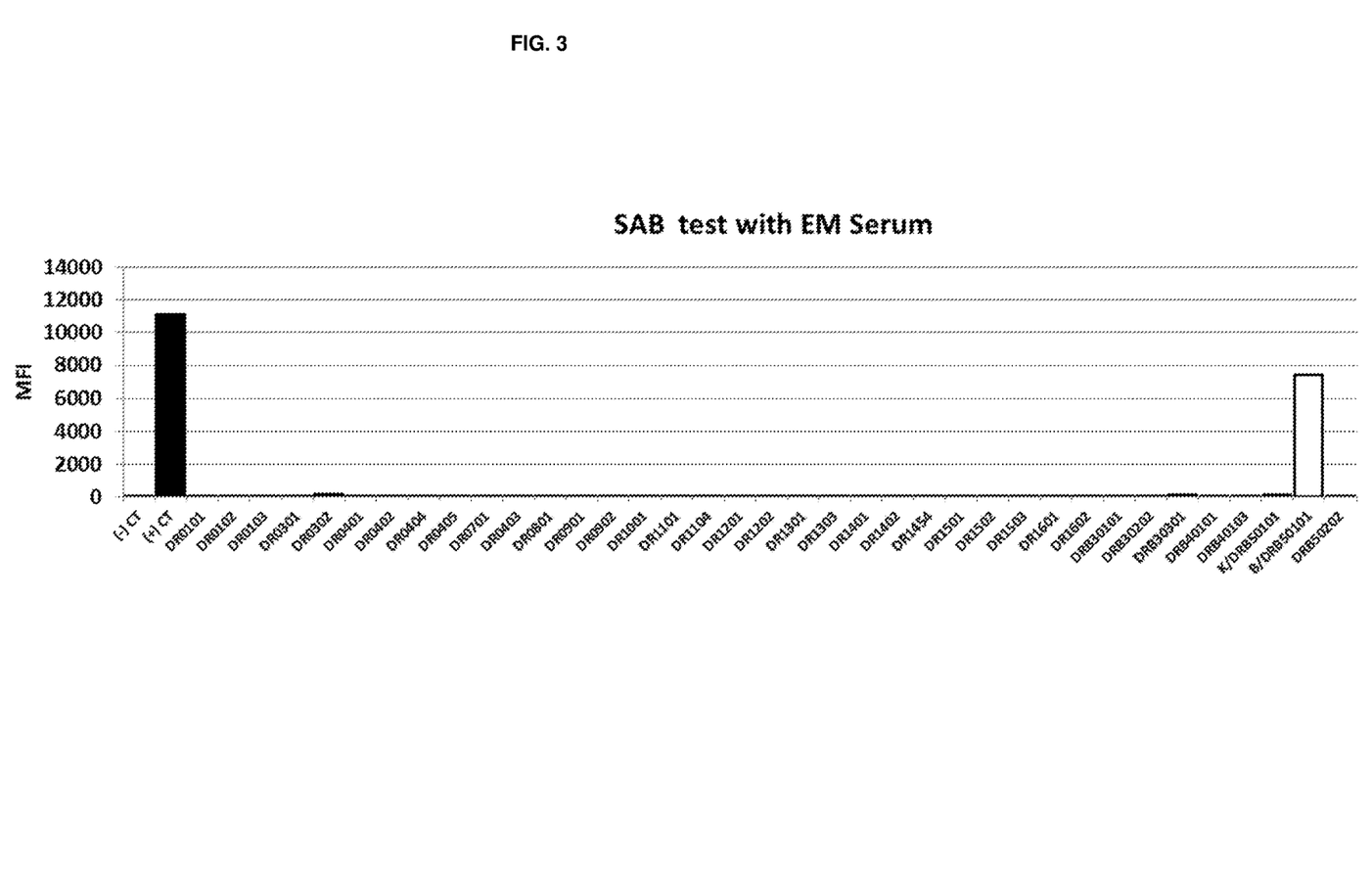
FIG. 3 depicts the reaction pattern of positive sera, EM, on the DRB5*01:01 antigen generated from either invariable chain producing recombinant host (B/DRB5*01:01) or from invariant chain deficient recombinant host (K/DRB5*01:01).

FIG. 3 depicts the reaction pattern of positive sera, EM, on the DRB5*01:01 antigen generated from either invariable chain producing recombinant host (B/DRB5*01:01) or from invariant chain deficient recombinant host (K/DRB5*01:01) and the results depicted in FIG. 3 show that recombinant DRB5*01:01 antigen from invariant chain producing B line host (B/DRB5*01:01) gave positive reactivity on EM serum while its counterpart produced by invariable deficient recombinant K line (K/DRB5*01:01) gives false negative reactivity.

Numerous modifications and variations in the practice of the invention are expected to occur to those skilled in the art upon consideration of the foregoing description on the presently preferred embodiments thereof. Consequently, the only limitations which should be placed upon the scope of the present invention are those that appear in the appended claims.

The following sequences referenced to herein are shown in the accompanying

```
Sequence Listing
SEQ ID NO. 1:
MRMATPLLM

SEQ ID NO. 2:
KPVSQMRMATPLLMRPM
```

What is claimed is:

1. A method of screening for antibodies that specifically bind an HLA Class II antigen in which a CLIP peptide is present in the peptide binding groove comprising the steps of:
preparing a panel comprising a solid-phase substrate having an HLA Class II antigen in which a CLIP peptide is present in the peptide binding groove immobilized or attached thereto, wherein the CLIP peptide is a subsequence of human CD74 invariant chain comprising MRMATPLLM (SEQ ID NO: 1);
obtaining a serum sample from a human subject,
contacting the panel with the serum sample, and
detecting binding of antibodies in said serum sample to the HLA Class II antigen in which a CLIP peptide is present in the peptide binding groove.

2. The method of claim 1 wherein the HLA Class II antigen in which a CLIP peptide is present in the peptide binding groove is prepared by the method of transfecting a host cell capable of expressing an HLA Class II antigen with a gene encoding the invariant chain and expressing said HLA Class II antigen.

3. The method of claim 1 wherein the HLA Class II antigen in which a CLIP peptide is present in the peptide binding groove is prepared by the method of transfecting a host cell which expresses the invariant chain with a gene expressing an HLA Class II antigen.

4. The method of claim 1 wherein the HLA Class II antigen in which a CLIP peptide is present in the peptide binding groove is prepared by the method of preparing an HLA Class II antigen and incubating said antigen with CLIP peptide under conditions selected to introduce said CLIP peptide into the antigen peptide binding groove.

5. The method of claim 1, further comprising the steps of:
preparing a panel comprising a second solid-phase substrate having said HLA class II antigen in which the peptide binding groove thereof is free of the CLIP peptide above a selected threshold;
contacting the said second panel with the serum sample, and
detecting binding of antibodies in the said serum sample to said HLA class II antigen in which the peptide binding groove thereof is free of the CLIP peptide above a selected threshold.

6. The method of claim 5 wherein the threshold is selected to avoid a false positive reaction.

7. The method of claim 4 wherein the solid-phase substrate is a microparticles, wherein the said panel comprises a multiplicity of microparticles, and wherein each microparticle presents at least one selected HLA antigen.

8. The method of claim 4 wherein binding of an antibody is detected using flow cytometry.

9. The method of claim 4 wherein antibody binding is detected with a secondary antibody.

10. The method of claim 9 wherein the secondary antibody comprises a label selected from the group consisting of a radioactive label, fluorescent label, enzymatic label, colorimetric label avidin label and biotin label.

11. The method of claim 4 wherein the human subject is a transplant or transfusion recipient.

12. The method of claim 4 wherein the human subject is a transplant or transfusion donor.

* * * * *

SEQUENCE LISTING

```
Sequence total quantity: 2
SEQ ID NO: 1              moltype = AA  length = 9
FEATURE                   Location/Qualifiers
REGION                    1..9
                          note = Synthetic Polypeptide
source                    1..9
                          mol_type = protein
                          organism = synthetic construct
SEQUENCE: 1
MRMATPLLM                                                              9

SEQ ID NO: 2              moltype = AA  length = 17
FEATURE                   Location/Qualifiers
REGION                    1..17
                          note = Synthetic Polypeptide
source                    1..17
                          mol_type = protein
                          organism = synthetic construct
SEQUENCE: 2
KPVSQMRMAT PLLMRPM                                                    17
```